(12) United States Patent
Gist et al.

(10) Patent No.: US 12,727,898 B2
(45) Date of Patent: Sep. 8, 2026

(54) MEDICAL SNARE

(71) Applicant: Merit Medical Systems, Inc., South Jordan, UT (US)

(72) Inventors: Jahi Gist, Barrington, IL (US); Zach Ingram, Rolling Meadows, IL (US); Riley Rapert, Lake Zurich, IL (US); Lillian Rhodes, Littleton, CO (US); Timothy Robert Smith, Butler, PA (US)

(73) Assignee: Merit Medical Systems, Inc., South Jordan, UT (US)

( * ) Notice: Subject to any disclaimer, the term of this patent is extended or adjusted under 35 U.S.C. 154(b) by 282 days.

(21) Appl. No.: 18/376,162

(22) Filed: Oct. 3, 2023

(65) Prior Publication Data

US 2024/0108369 A1 Apr. 4, 2024

Related U.S. Application Data

(60) Provisional application No. 63/412,692, filed on Oct. 3, 2022.

(51) Int. Cl.
*A61B 17/221* (2006.01)
*A61B 17/00* (2006.01)

(52) U.S. Cl.
CPC .. *A61B 17/221* (2013.01); *A61B 2017/00867* (2013.01); *A61B 2017/2212* (2013.01)

(58) Field of Classification Search
CPC ........ A61B 17/00234; A61B 17/00389; A61B 17/1214; A61B 17/221; A61B 17/22031;
(Continued)

(56) References Cited

U.S. PATENT DOCUMENTS

| | | | |
|---|---|---|---|
| 5,562,678 | A | 10/1996 | Booker |
| 6,136,005 | A | 10/2000 | Goode et al. |

(Continued)

FOREIGN PATENT DOCUMENTS

| | | | |
|---|---|---|---|
| DE | 102005042216 | A1 | 3/2007 |
| DE | 102006053448 | A1 | 6/2008 |

(Continued)

OTHER PUBLICATIONS

Mediterra, "Snares", View the product range, retrieved from the internet Jan. 27, 2022, URL: https://www.mediterra.com.cy/productitems-taxonomy/vascular-surgery-intervention/snares-vascular-surgery-intervention/.

(Continued)

*Primary Examiner* — Kankindi Rwego
(74) *Attorney, Agent, or Firm* — Dorsey & Whitney LLP

(57) ABSTRACT

Snares for retrieval of medical devices from the body of an animal, medical assemblies, kits, and methods of retrieving a medical device from the body of an animal are described. An example snare comprises an outer sheath defining an outer sheath lumen; an elongate member disposed in the outer sheath lumen and having a longitudinal axis and at least one elongate member lumen; a capture member disposed and axially movable within the at least one elongate member lumen, the capture member defining a capture loop having a throat region and a portion extending along a plane that is perpendicular to the longitudinal axis of the elongate member; and a threader member disposed and axially movable within the at least one elongate member lumen, the threader member defining a threader loop. A handle includes a rotatable control member for deflecting a distal end of the outer sheath.

20 Claims, 6 Drawing Sheets

(58) Field of Classification Search
CPC .... A61B 17/32056; A61B 2017/00349; A61B 2017/00353; A61B 2017/00358; A61B 2017/00867; A61B 2017/1205; A61B 2017/2212; A61B 2017/2215; A61B 2017/2217; A61B 2017/22034; A61B 2017/22035; A61F 2/01; A61F 2/011; A61F 2/24; A61F 2/2427; A61F 2/243; A61F 2/2433; A61F 2/2436; A61F 2/2439; A61F 2/95; A61F 2/9517; A61F 2/954; A61F 2/958; A61F 2/962; A61F 2002/9528; A61F 2002/9534; A61M 2025/0036; A61M 2025/0037
USPC .......................................................... 606/129
See application file for complete search history.

(56) References Cited

U.S. PATENT DOCUMENTS

| | | | | |
|---|---|---|---|---|
| 7,359,756 | B2 | 4/2008 | Goode | |
| 7,651,504 | B2 | 1/2010 | Goode et al. | |
| 8,192,430 | B2 | 6/2012 | Goode et al. | |
| 8,628,540 | B2 | 1/2014 | Freudenthal | |
| 9,592,036 | B2 | 3/2017 | Kappel et al. | |
| 9,700,345 | B2 | 7/2017 | Kappel et al. | |
| 9,731,113 | B2 | 8/2017 | Grace et al. | |
| 9,936,965 | B2 | 4/2018 | Goode et al. | |
| 9,999,432 | B2 | 6/2018 | Kramann | |
| 10,004,522 | B2 | 6/2018 | Kramann | |
| 10,105,533 | B2 | 10/2018 | Grace | |
| 10,188,412 | B2 | 1/2019 | Booker et al. | |
| 10,687,836 | B2 | 6/2020 | Taylor et al. | |
| 10,960,216 | B2 | 3/2021 | Shuros et al. | |
| 2011/0098720 | A1* | 4/2011 | Taylor | A61B 17/221 606/129 |
| 2015/0051615 | A1* | 2/2015 | Schmidt | A61N 1/3756 606/129 |
| 2015/0157344 | A1 | 6/2015 | Tah et al. | |
| 2020/0113602 | A1 | 4/2020 | Drake et al. | |
| 2020/0330112 | A1 | 10/2020 | Verma et al. | |

FOREIGN PATENT DOCUMENTS

| | | | |
|---|---|---|---|
| DE | 202013103881 | U1 | 1/2015 |
| EP | 2489313 | A1 | 8/2012 |
| RU | 2698990 | C2 | 9/2019 |
| WO | 2007046953 | A2 | 4/2007 |
| WO | 2021180550 | A1 | 9/2021 |

OTHER PUBLICATIONS

Cook Medical, “Needle’s Eye Snare, Transvenous Retrieval Set”, Product Brochure, retrieved from the internet Jan. 18, 2022, URL: https://cdnnamsseuspwsprod.azureedge.net/data/resources/LM-D59540-EN-F_M3_1620141213963.pdf.

Bracke et al., “The Needle’s Eye Snare as a primary tool for pacing lead extraction”, European Society of Cardiology, (2013), vol. 15, Issue 7, pp. 1007-1012.

The Extended European Search Report, Application No. 23201493.6, dated Feb. 20, 2024.

* cited by examiner

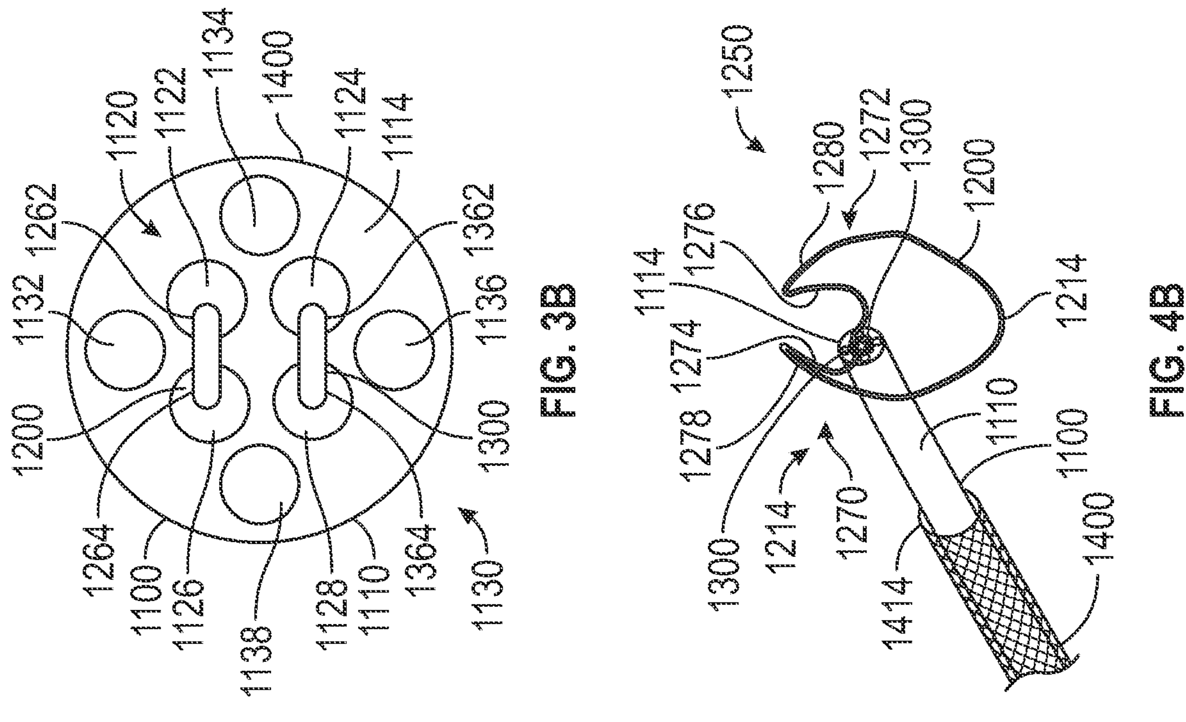
FIG. 3B
FIG. 4B
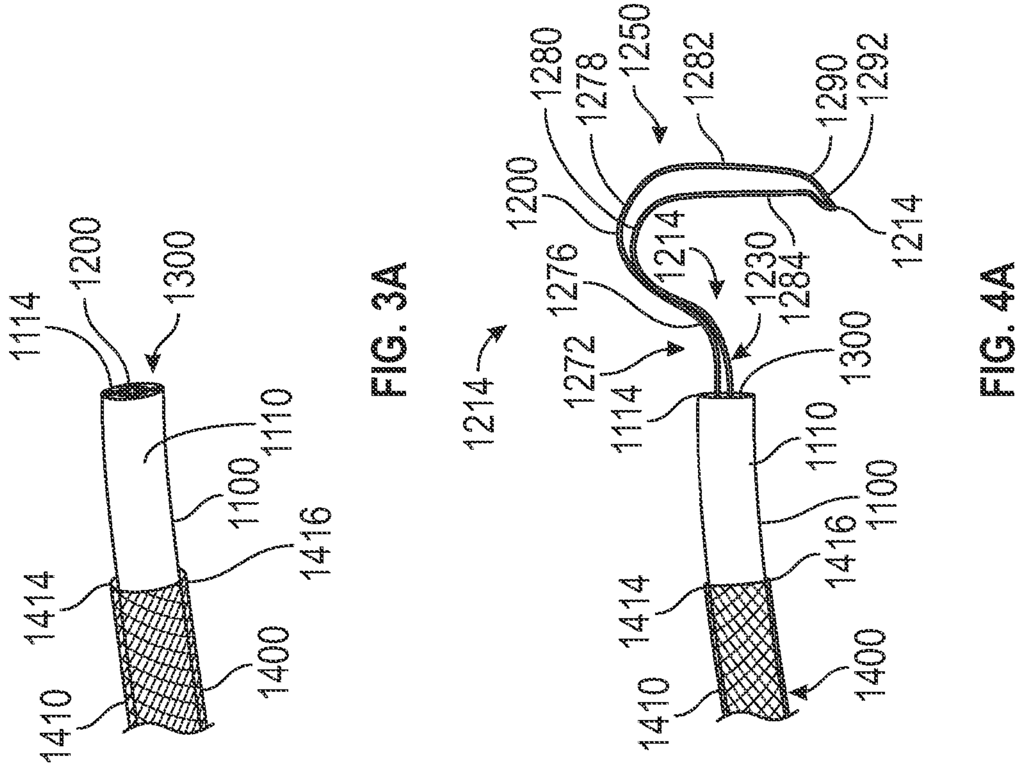
FIG. 3A
FIG. 4A

MEDICAL SNARE

FIELD

The disclosure relates to medical devices. More particularly, the disclosure relates to snares useful in the retrieval of other medical devices, such as pacemaker and defibrillator leads, from the body of an animal, such as a human being. The disclosure also relates to medical assemblies, kits, and methods.

BACKGROUND

Medical snares enable the retrieval of medical devices and other indwelling objects from within the body of an animal. For example, snares are frequently used to retrieve pacemaker and defibrillator lead fragments and leadless devices. While the art includes several examples of snares useful in the retrieval of these devices, existing snares lack desired precision in the deployment and manipulation of individual components involved in capturing a device to be retrieved. Use of these known devices can prolong the retrieval procedure without providing a corresponding positive impact on patient outcomes.

A need exists, therefore, for improved snares for retrieval of medical devices from the body of an animal. A need also exists for snare-related medical assemblies and kits, and methods of retrieving a medical device from the body of an animal.

BRIEF SUMMARY OF SELECTED EXAMPLES

Various example snares are described.

An example snare comprises an outer sheath defining an outer sheath lumen; an elongate member disposed in the outer sheath lumen and having a longitudinal axis and at least one elongate member lumen; a capture member disposed and axially movable within the at least one elongate member lumen, the capture member defining a capture loop having a throat region and a portion extending along a plane that is perpendicular to the longitudinal axis of the elongate member; and a threader member disposed and axially movable within the at least one elongate member lumen, the threader member defining a threader loop.

Another example snare comprises an outer sheath defining an outer sheath lumen; an elongate member disposed in the outer sheath lumen and having a longitudinal axis and at least one elongate member lumen; a capture member disposed and axially movable within the at least one elongate member lumen, the capture member defining a capture loop having a throat region, a first portion extending along a plane that is perpendicular to the longitudinal axis of the elongate member, and a second portion extending from the first portion and along a plane disposed at a non-parallel and non-orthogonal angle to the longitudinal axis of the elongate member; and a threader member disposed and axially movable within the at least one elongate member lumen, the threader member defining a threader loop.

An example snare comprises an outer sheath defining an outer sheath lumen; an elongate member having a longitudinal axis and disposed and axially movable within the outer sheath lumen, the elongate member having an elongate member proximal end, an elongate member distal end, and an elongate member main body extending between the elongate member proximal end and the elongate member distal end and having at least one elongate member lumen extending from the elongate member proximal end to the elongate member distal end; a capture member disposed and axially movable within the at least one elongate member lumen, the capture member having a capture member proximal end and a capture member distal end, the capture member distal end defining a capture loop having a throat region, a first portion extending along a plane that is perpendicular to the longitudinal axis of the elongate member, and a second portion extending from the first portion, the second portion including the capture member distal end and extending along a plane disposed at a non-parallel and non-orthogonal angle to the longitudinal axis of the elongate member; a threader member disposed and axially movable within the at least one elongate member lumen, the threader member having a threader member proximal end and a threader member distal end, the threader member distal end defining a threader loop; and a handle attached to the elongate member, the handle including a plunger attached to the threader member.

An example kit comprises a snare according to an embodiment and an introducer sheath disposed within a container.

An example method of retrieving a medical device from the body of an animal comprises navigating a distal end of a snare according to an embodiment to a location within a vessel within the body of an animal at which a device to be retrieved is located; distally advancing a capture member of the snare within the elongate member of the snare such that a loop of the capture member exits the elongate member and a portion of the loop lies on a plane that is perpendicular to, or substantially perpendicular to, a lengthwise axis of the elongate member; manipulating the capture member loop such that a portion of the device to be retrieved is positioned within a throat region of the capture member loop; distally advancing a threader member of the snare within the elongate member of the snare such that a loop of the threader member passes through the capture member loop; retracting the capture member within the elongate member of the snare such that the capture member loop tightens around a portion of the device to be retrieved; retracting the elongate member such that the capture member, threader member, and the device to be retrieved move through the body vessel and exit the body of the animal.

Additional understanding of the inventive snares, medical assemblies, kits, and methods can be obtained by reviewing the detailed description of selected examples, below, and the referenced drawings.

DESCRIPTION OF FIGURES

FIG. 3A is a side view, partially broken away, of the example snare illustrated in FIG. 1. The capture loop and threader loop are both illustrated in a non-extended position.

FIG. 3B is a magnified end view of the example snare illustrated in FIG. 3A. The capture loop and threader loop are both illustrated in a non-extended position.

FIG. 4A is a side view, partially broken away, of the example snare illustrated in FIG. 1. The capture loop is illustrated in an extended position.

FIG. 4B is an end view of the example snare illustrated in FIG. 4A. The capture loop is illustrated in an extended position; the threader loop is illustrated in a non-extended position.

DETAILED DESCRIPTION OF SELECTED EXAMPLES

The following detailed description and the appended drawings describe and illustrate various example snares, medical assemblies, kits, and methods. The description and illustration of these examples enable one skilled in the art to make and use examples of the inventive snares, medical assemblies, and kits, and to practice the inventive methods. They do not limit the scope of the claims in any manner.

Figure 1:
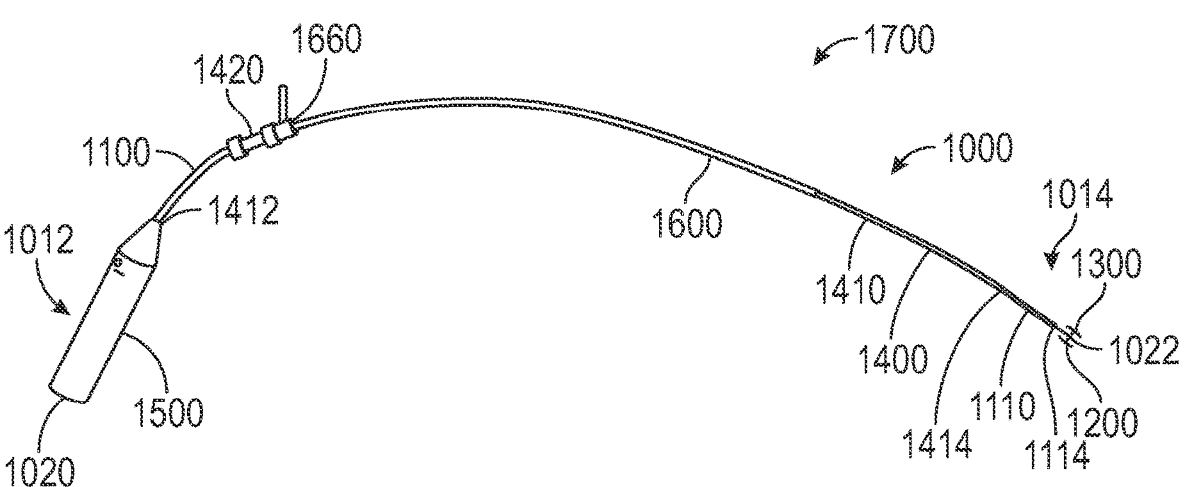
FIG. 1 is a perspective view of an example medical assembly that includes an example snare.
Figure 2:
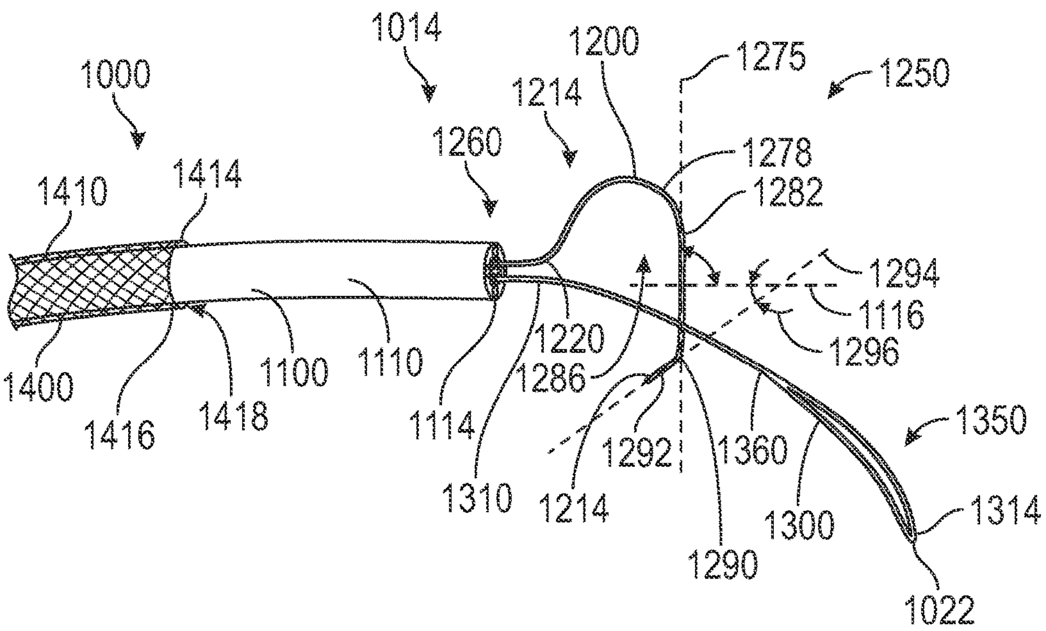
FIG. 2 is a side view, partially broken away, of the distal end portion of the example snare illustrated in FIG. 1. The capture loop and threader loop are both illustrated in an extended position.
Figure 5B:
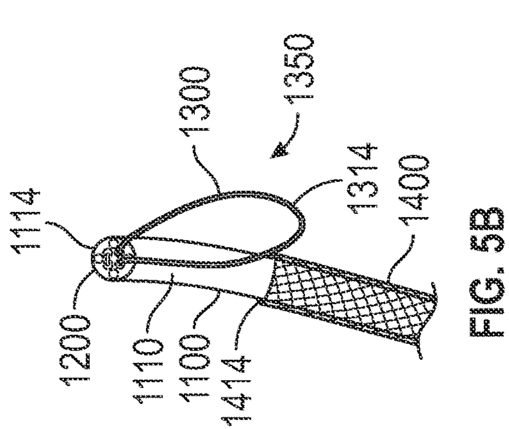
FIG. 5B is an end view of the example snare illustrated in FIG. 5A. The threader loop is illustrated in an extended position; the capture loop is illustrated in a non-extended position.
Figure 6B:
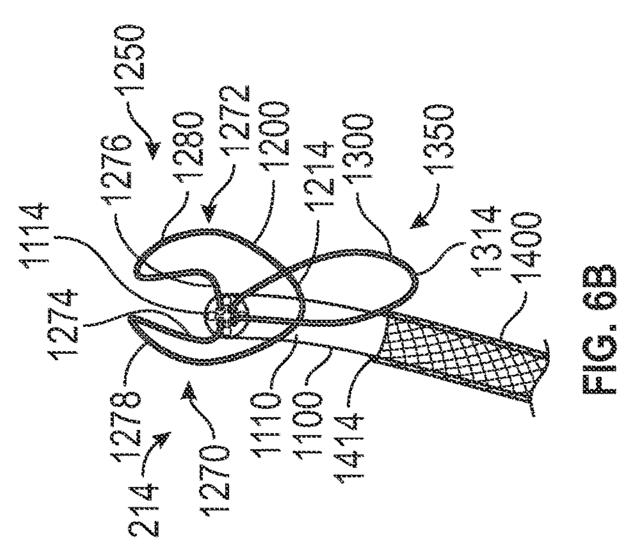
FIG. 6B is an end view of the example snare illustrated in FIG. 1. Each of the capture loop and the threader loop is illustrated in an extended position.
Figure 5A:
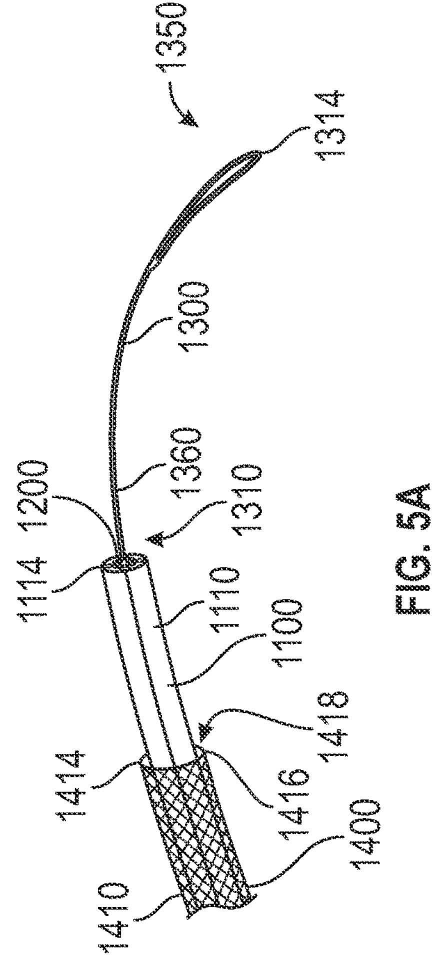
FIG. 5A is a side view, partially broken away, of the example snare illustrated in FIG. 1. The threader loop is illustrated in an extended position; the capture loop is illustrated in a non-extended position.
Figure 6A:
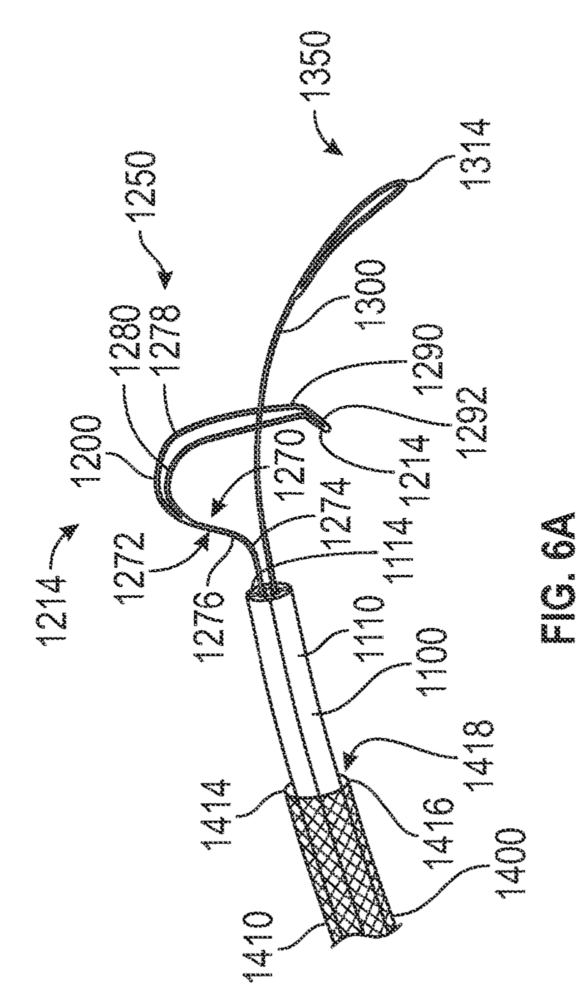
FIG. 6A is a side view, partially broken away, of the example snare illustrated in FIG. 1. Each of the capture loop and the threader loop is illustrated in an extended position.
Figures 7, 8:
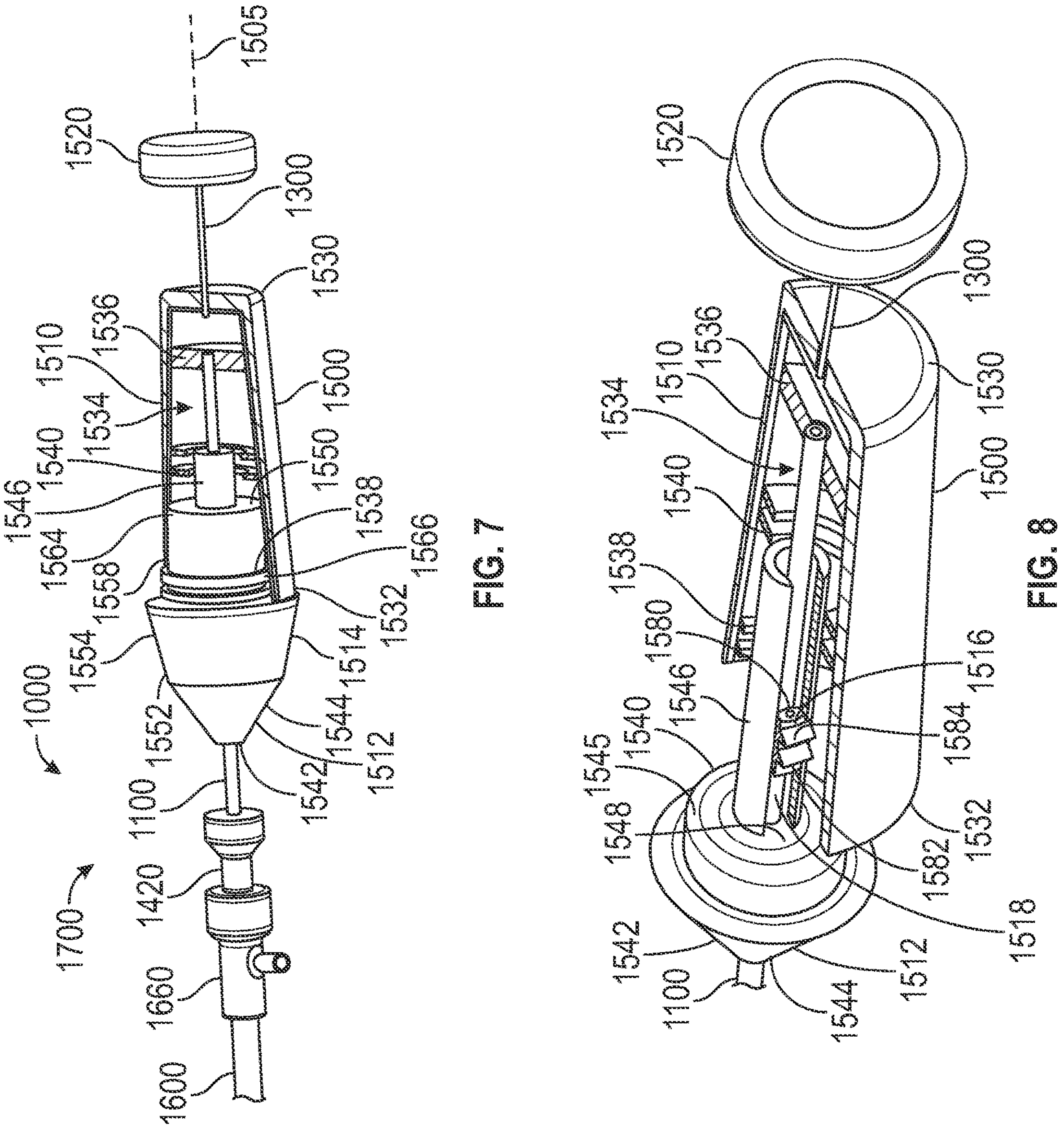
FIG. 7 is a side view of a portion of the medical assembly illustrated in FIG. 1. A portion of the handle has been broken away to show internal structure.
FIG. 8 is a perspective view, partially broken away, of the handle illustrated in FIG. 7.
Figure 9:
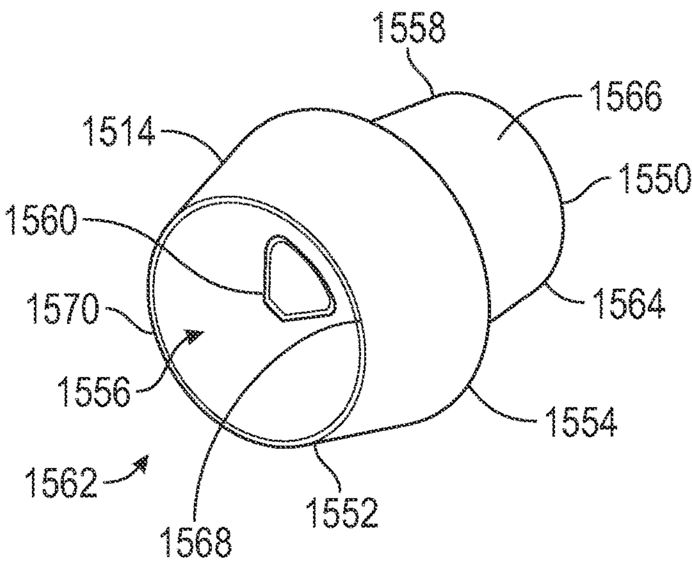
FIG. 9 is a perspective view of the knob of the handle illustrated in FIG. 8.

Each of FIGS. 1, 2, 3A, 3B, 4A, 4B, 5A, 5B, 6A, 6B, and 7 illustrate a first example snare 1000 or a portion of the first example snare 1000. FIG. 1 illustrates the snare 1000 as a component in a medical assembly 1700. FIG. 2 illustrates a distal portion of the snare 1000 and shows a structural arrangement of the components of the snare 1000. Each of FIGS. 3A, 3B, 4A, 4B, 5A, 5B, 6A, and 6B illustrates a structural arrangement of various components of the snare 1000 during a particular stage of use of the snare 1000. FIG. 7 illustrates the handle 1500 of the snare 1000.

The snare 1000 includes an elongate member 1100 disposed within, extends through, and is axially movable relative to an outer sheath 1400. A capture member 1200 is disposed within, extends along at least a portion of, and is axially movable relative to the elongate member 1110. A threader member 1300 is also disposed within, extends along at least a portion of, and is axially movable relative to the elongate member 1110. A handle 1500 is attached to the elongate member 1100. As best illustrated in FIG. 1, the elongate member 1100 and outer sheath 1400 can extend through an introducer sheath 1600 to form a medical assembly 1700.

The snare 1000 has a proximal end 1012 and a distal end 1014. The terminal surface 1020 of the proximal end 1012 is formed by the handle 1500. The terminal surface 1022 of the distal end 1014 is alternatively formed by various components, including the elongate member 1100, capture member 1200, and threader member 1300, depending on the relative structural arrangement of these components in the snare 1000 at any given time. In FIGS. 1 and 2, the threader member 1300 is in an extended position relative to the elongate member 1100 and, as such, the threader member 1300 defines the terminal surface 1022 of the distal end 1014 of the snare 1000 in these figures.

The elongate member 1100 has a main body 1110 that extends from a proximal end 1112 to a distal end 1114 along a lengthwise axis 1116. As best illustrated in FIG. 3B, the main body 1110 defines multiple lumens 1122, 1124, 1126, 1128, 1132, 1134, 1136, 1138, each of which extends from the proximal end 1112 to the distal end 1114. A first set 1120 of lumens is disposed centrally in the main body 1110 relative to the longitudinal axis 1116; a second set 1130 of lumens is disposed peripherally relative to the longitudinal axis 1116. The lumens 1122, 1124, 1126, 1128 of the first set 1120 of lumens are disposed radially inward of the lumens 1132, 1134, 1136, 1138 of the second set 1130 of lumens, while the lumens 1132, 1134, 1136, 1138 of the second set 1130 of lumens are disposed radially outward from the lumens 1122, 1124, 1126, 1128 of the first set 1120 of lumens.

As best illustrated in FIG. 3B, the main body 1110 in the illustrated example is a solid body that defines each of the lumens 1122, 1124, 1126, 1128, 1132, 1134, 1136, 1138. In this embodiment, the main body 1110 can be an extruded member, for example, with each of the lumens 1122, 1124, 1126, 1128, 1132, 1134, 1136, 1138 formed during the extrusion process or otherwise. In other example snares, one or more of the lumens in the main body comprises a separate member, such as a cannula, extending through the main body, such as from the proximal end to the distal end. In these examples, the main body has a circumferential wall that defines a lumen within which the cannula or cannulae are disposed. The circumferential wall comprises one or more polymeric layers and advantageously includes one or more reinforcing layers, such as a coil or mesh, extending along a portion or the entire axial length of the main body. In some examples, all of the lumens comprise separate members extending through the main body from the proximal end to the distal end. In one particular example, each lumen comprises a metal cannula extending through a central lumen defined by a plastic main body of the elongate member. In this example, the cannula are arranged in the same structural arrangement as the lumens 1122, 1124, 1126, 1128, 1132, 1134, 1136, 1138 are arranged in FIG. 3B, although other structural arrangements are possible. In some embodiments, one or more pull wires are connected to a portion of the handle and individually extend through a lumen and attach to a distal portion of the elongate member 1100. In these embodiments, this structural arrangement enables steering of the distal end 1114 of the elongate member 1100 by manipulating the handle 1500 to cause movement of the distal end 1114 of the elongate member 1100 through the one or more pull wires.

The capture member 1200 has a main body 1210 extending between proximal 1212 and distal 1214 ends. As best illustrated in FIGS. 4A, 4B, 6A, and 6B, the main body 1210 in the illustrated example is formed by a single elongate member 1260 doubled back to form a loop 1250 at the distal end 1214. As best illustrated in FIG. 3B, individual legs 1262, 1264 of the capture member 1200 are disposed in individual lumens 1122, 1126 of the elongate member 1110, providing proximal leg ends 1266, 1268 at the proximal end 1212 of the capture member 1200, opposite the loop 1250 at the distal end 1214 of the capture member 1200. This structural arrangement is considered advantageous at least because it provides proximal leg ends 1262, 1264 that can be independently attached to the handle 1500.

As best illustrated in FIGS. 4A, 4B, 6A, and 6B, a distal portion 1270, 1272 of each leg 1262, 1264 extends beyond the distal end 1114 of the elongate member 1110 as the capture member 1200 is advanced distally relative to elongate member 1100. The distal portions 1270, 1272 join at the distal end 1214 of the capture member 1200, cooperatively forming loop 1250. When loop 1250 is extended beyond the distal end 1114 of the elongate member 1110, the distal portion 1270, 1272 of each leg 1262, 1264 adopts a configuration having a first curve 1274, 1276 and a second curve 1278, 1280 such that the respective leg 1262, 1264 first extends away from the longitudinal axis 1116 of the elongate member 1100 and, moving distally along the respective leg 1262, 1264, extends toward and across the longitudinal axis 1116. Also, as best illustrated in FIG. 2, a portion 1282, 1284 of the distal portion 1270, 1272 of each leg 1262, 1264 lies on a plane 1275 that is perpendicular to, or substantially perpendicular to, the longitudinal axis 1116 of the elongate member 1100. This structural arrangement forms a throat region 1286 in loop 1250 that is bounded by the first curves 1274, 1276, the second curves 1278, 1280, and the portions 1282, 1284 perpendicular to, or substantially perpendicular to the longitudinal axis 1116 of the elongate member 1100.

In the illustrated embodiment, the distal end 1214 of the capture member 1200, formed by the converging the distal portions 1270, 1272 of legs 1262, 1264, includes a bend 1290 forming a flat portion 1292 of the loop 1250 that lies on a plane 1294 disposed at an angle 1296 to the longitudinal axis 1116 of the elongate member 1100. Inclusion of bend 1290, flat portion 1292, and angle 1296 is considered advantageous at least because these structures cooperate to provide a structural stop for items positioned within the throat region 1286, such as a medical device during retrieval using the snare 1000. Inclusion of bend 1290, flat portion 1292, and angle 1296 is also considered advantageous at least because it provides a structure within which a portion of a medical device being retrieved, such as a docking hub of a pacemaker lead, can be seated during removal of the lead. Considering this benefit, it is considered important that, if included, angle 1296 is less than or equal to about 90 degrees. An angle of less than or equal to about 90 degrees and greater than or equal to about 0 degrees is also considered advantageous. An angle of less than or equal to about 60 degrees and greater than or equal to about 15 degrees is also considered advantageous. An angle of less than or equal to about 45 degrees and greater than or equal to about 30 degrees is also considered advantageous. An angle equal to about 45 degrees is considered particularly advantageous.

While the capture member 1200 in the illustrated example is an elongate member 1270 configured to have individual legs 1262, 1264 that extend through individual lumens 1122, 1126 within the elongate member 1100, a capture member can have a single leg with a loop formed on its distal end. In these embodiments, the leg of the capture member is disposed through only a single lumen of the elongate member of the snare. Also, while the capture member 1200 in the illustrated example is formed of a wire have a circular cross-sectional shape, other cross-sectional shapes can be used, including ovoid, rectangular, and square cross-sectional shapes.

The threader member 1300 has a main body 1310 extending between proximal (not visible in Figures) and distal 1314 ends. As best illustrated in FIGS. 5A, 5B, 6A, and 6B, the main body 1310 in the illustrated example is formed by a single elongate member 1360 doubled back to form a loop 1350 at the distal end 1314. As best illustrated in FIG. 3B, individual legs 1362, 1364 of the elongate member 1360 are disposed in individual lumens 1124, 1128 of the elongate member 1110, providing proximal leg ends (not visible in Figures) at the proximal end of the threader member 1300, opposite the loop 1350 at the distal end 1314 of the threader member 1300. This structural arrangement is considered advantageous at least because it provides proximal leg ends that can be independently attached to the handle 1500.

As best illustrated in FIGS. 5A, 5B, 6A, and 6B, a distal portion 1370, 1372 of each leg 1362, 1364 extends beyond the distal end 1114 of the elongate member 1110 as the threader member 1300 is advanced distally relative to elongate member 1100. The distal portions 1370, 1372 join at the distal end 1314 of the threader member 1300, cooperatively forming loop 1350. When loop 1350 is extended beyond the distal end 1114 of the elongate member 1110, the distal portion 1370, 1372 of each leg 1362, 1364 adopts a configuration having a curve 1374, 1376 that slightly extends away from the longitudinal axis 1116 of the elongate member 1100. As best illustrated in FIGS. 2 and 6A, the curves 1374, 1376 are shaped such that the distal end 1314 and loop 1350 extend through the loop 1250 of the capture member 1200 when the loop 1250 is fully formed axially beyond the distal end 1114 of the elongate member 1110. This structural configuration is considered advantageous at least because it ensures that the loop 1350 of the threader member 1300 extends through the loop 1250 of the capture member 1250 as the loop 1350 of the threader member 1300 is axially extended beyond the distal end 1114 of the elongate member 1110 after the loop 1250 of the capture member 1250 is fully formed axially extended beyond the distal end 1114 of the elongate member 1110, effectively closing the throat region 1286 in loop 1250 of the capture member 1200, effectively capturing anything disposed within the throat region 1286, such as a medical device being retrieved from a body of an animal.

As best illustrated in FIG. 5B, the threader member 1300 can be axially extended beyond the distal end 1114 of the elongate member 1100 while the capture member remains within the elongate member 1100. The loop 1350 of the threader member, for example, can itself be used to engage another structure, such as a medical device to be retrieved from the body of an animal.

While the threader member 1300 in the illustrated example is an elongate member 1370 configured to have individual legs 1362, 1364 that extend through individual lumens 1124, 1128 within the elongate member 1100, a threader member can have a single leg with a loop formed on its distal end. In these embodiments, the leg of the threader member is disposed through only a single lumen of the elongate member of the snare. Also, while the threader member 1300 in the illustrated example is formed of a wire have a circular cross-sectional shape, other cross-sectional shapes can be used, including ovoid, rectangular, and square cross-sectional shapes.

The outer sheath 1400 is an elongate member having a main body 1410 extending between proximal 1412 and distal 1414 ends. The main body 1410 has a circumferential wall 1416 that defines a lumen 1418 within which the elongate member 1100 is disposed. The outer sheath 1400 in the illustrated example includes a hub 1420 on its proximal end 1412. Advantageously, the circumferential wall 1416 of the outer sheath comprises one or more polymeric layers. The circumferential wall 1416 can also include one or more reinforcing layers, such as a coil or mesh. It is considered advantageous, though, to include an outer sheath that lacks a reinforcement coil or mesh in a snare having an elongate member having a reinforcement coil or mesh in its main body, as described above. This structural arrangement allows the elongate member to manipulate the sheath, such as through deflection through pull wire manipulation.

As best illustrated in FIGS. 7 and 8, the handle 1500 includes a housing 1510, a nose cone 1512, a control member 1514, a fin 1516, a pull wire (not illustrated in the Figures) connected to fin 1516 and distal end 1414 of outer sheath 1400, and a plunger 1520. The handle 1500 enables a user to independently extend and retract the capture member 1200 and the threader member 1300 and to deflect the distal end 1414 of the outer sheath 1400 during use of the snare 1000. These actions enable capturing and retrieving a medical device to be retrieved, such as a lead, using the snare 1000. Control member 1514 is removed from handle 1500 in FIG. 8 for illustrative purposes.

The housing 1510 has a proximal end 1530 and a distal end 1532 and defines a cavity 1534. Each of FIGS. 7 and 8 illustrates the housing 1510 with a portion removed to reveal the cavity 1534 and internal structure. A support member 1536 is disposed in the cavity 1534 adjacent the proximal end 1530, a first set of support ribs 1538 is disposed in the cavity 1534 adjacent the distal end 1532, and a second set of support ribs 1540 is disposed within the cavity 1534 axially between the support member 1536 and the first set of support ribs 1538.

As best illustrated in FIG. 8, the nose cone 1512 has a proximal end 1540 and a distal end 1542. The distal end 1542 defines a conical portion 1544. A boss 1545 extends proximally from the conical portion 1544. An elongate body 1546 extends proximally from the boss 1545 and defines slot 1548 that receives fin 1516, as described below. Also as described below, control member 1514 fits over boss 1544 and elongate body 1546 extends through the control member 1514.

Control member 1514 has a proximal end 1550 and a distal end 1552. The distal end 1552 defines a frustoconical portion 1554. A sidewall 1556 in the frustoconical portion 1554 defines distal recess 1556 that receives boss 1545 of nose cone 1512. A boss 1558 extends proximally from the frustoconical portion 1554 and defines passageway 1560 that extends through the boss 1558, opening to the distal recess 1556 and the proximal end 1550 of the control member 1514 to cooperatively define a passageway 1562 that extends through the entire control member 1514 from the proximal end 1550 to the distal end 1552. As best illustrated in FIG. 7, the outer surface 1564 of boss 1558 defines circumferential projection 1566 that sits between the ribs of the first set of support ribs 1538 defined by housing 1510. Inner surface 1568 of the passageway 1560 of the boss 1558 defines thread 1570 that mates with teeth 1582, 1584 of fin 1516, as described below.

As best illustrated in FIG. 8, fin 1516 seats in slot 1548 of nose cone 1512. Fin 1516 defines a lumen 1580 and first 1582 and second 1584 teeth that mesh with thread 1570 on the inner surface 1568 of the of the boss 1558 of the control member 1514. Fin 1516 is axially moveable within slot 1548 and is attached to pull wire (not illustrated in Figures). Rotational movement of control member 1514 results in axial movement of fin 1516 along slot 1548 as a result of the meshed relationship of teeth 1582, 1584 and thread 1570.

Control member 1514 is rotatable along the lengthwise axis 1505 of the handle 1500. Referring to FIG. 7, a user can manually apply a force to one side of the frustoconical portion 1554, such as by pressing a thumb or finger on the frustoconical portion 1554 and moving the thumb or finger in a desired direction. In response, control member 1514 rotates in place along lengthwise axis 1505 of the handle 1500. Boss 1558 rotates within cavity 1534 of the housing 1510 during this rotation of control member 1514. Circumferential projection 1566 and the ribs of the first set of ribs 1538 maintain control member 1514 in its captive position relative to housing 1510 during rotation. Internally and in response to rotation of control member 1514, thread 1570 and teeth 1582, 1584 interact to urge fin 1516 to move axially within slot 1548, creating axial movement of element(s) attached to fin, such as outer sheath 1400 as described below. Control member 1514 can be configured to have any desired rotational orientation with respect to the result of axial movement of fin 1516 in slot 1548. In the illustrated example, clockwise rotation of the control member 1514 results in distally directed movement of fin 1516 in slot 1548 and deflection of a pull wire 1518 attached to fin 1516, and the distal end 1414 of the outer sheath 1400, in a first direction, while counterclockwise rotation of the control member 1514 results in proximally directed movement of fin 1516 in slot 1548 and deflection of pull wire 1518, and the distal end 1414 of the outer sheath 1400, in a second, opposite direction. In this example, clockwise rotation of control member 1514 deflects the distal end 1414 of the outer sheath 1400 off axis and counterclockwise rotation of control member 1514 returns the distal end 1414 of the outer sheath 1400 to its on axis position.

The plunger 1520 is attached to the threader member 1300 and can be used as a handle to independently extend and retract the threader member 1300. As best illustrated in FIGS. 1 and 2, the elongate member 1100 and outer sheath 1400 can extend through an optional introducer sheath 1600 to form a medical assembly 1700. In these examples, the introducer sheath 1600 is a tubular member defining a lumen through which the distal ends 1114, 1414 of the elongate member 1100 and outer sheath 1400, respectively, can be advanced. The introducer sheath 1600 can include additional components, such as hemostatic valve 1660.

The components of a snare according to an embodiment may be manufactured from a variety of different materials, including conventional materials for minimally-invasive interventional medical devices such as catheters, sheaths, and guidewires. Non-limiting examples of materials include vinyl, also known as polyvinyl chloride (PVC), rubber, latex, silicone, siliconized latex, and silicone elastomers. However, it should be appreciated that one skilled in the art can select alternative materials appropriate for medical devices within the scope of this disclosure. The capture member and threader member are advantageously formed of a shape memory material, such as a nickel titanium alloy, and formed so that the respective loops of these members return to the structural configurations described when extended axially beyond the distal end of the elongate member of the snare.

A snare according to an embodiment can have any suitable length. A skilled artisan can select a suitable length for a snare according to a particular embodiment based on various considerations, such as an intended use of the snare or the expected dimensions of a body vessel within which the snare is intended to be used. For example, the inventors have determined that, for a snare intended for use in a method of retrieving a medical device, such as a pacer lead, from the body of an animal, a length of greater than about 100 cm is suitable at least because this length provides sufficient length for a user to manipulate the snare to retrieve a pacer lead in the body of an animal through a femoral approach. Other lengths considered suitable include, but are not limited to, a length of greater than about 100 cm but less than about 150 cm, a length of greater than about 110 cm but less than about 140 cm, and a length of greater than about 120 cm but less than about 130 cm.

In snares according to some embodiments, the outer sheath is adapted to be temporarily locked to the capture member to prevent relative axial movement between the outer sheath and the capture member. This structural arrangement is considered advantageous at least because it facilitates a tandem approach technique in procedures in which the snare is used.

Figure 10:
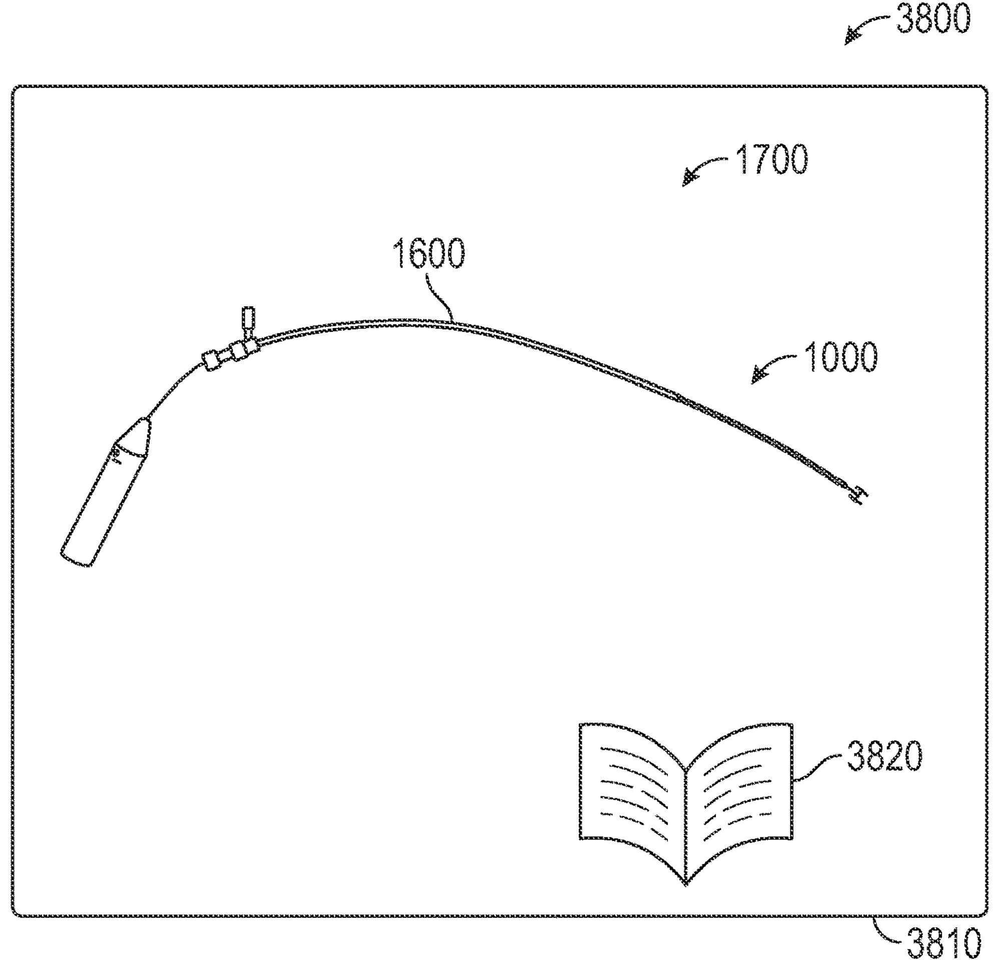
FIG. 10 illustrates an example kit.

FIG. 10 illustrates an example kit 3800. The kit 3800 is useful in forming a medical assembly, such as medical assembly 1700 illustrated in FIG. 1 and described above, and in methods of retrieving a medical device from the body of an animal, such as the example method 4000 described illustrated in FIG. 10 and described below.

Kit 3800 includes snare 1000 and introducer sheath 1600 disposed within a container 3810. Instructions for use 3820 of the snare 1000, the introducer sheath 1600, the medical assembly 1700 of the snare 1000 and introducer sheath 1600, or any one or more of these components can be included in the kit 3800.

While the illustrated kit 3800 includes the first example snare 1000, a kit according to an embodiment can include a snare according to any embodiment. For example, a kit according to an embodiment can include a snare that lacks pull wires if desired. Similarly, while the illustrated kit 3800 includes the introducer sheath 1600 illustrated in FIG. 1 as a component of medical assembly 1700, a kit according to an embodiment can include any introducer sheath suitable for introducing the snare of the kit into a body vessel of an animal.

Figure 11:
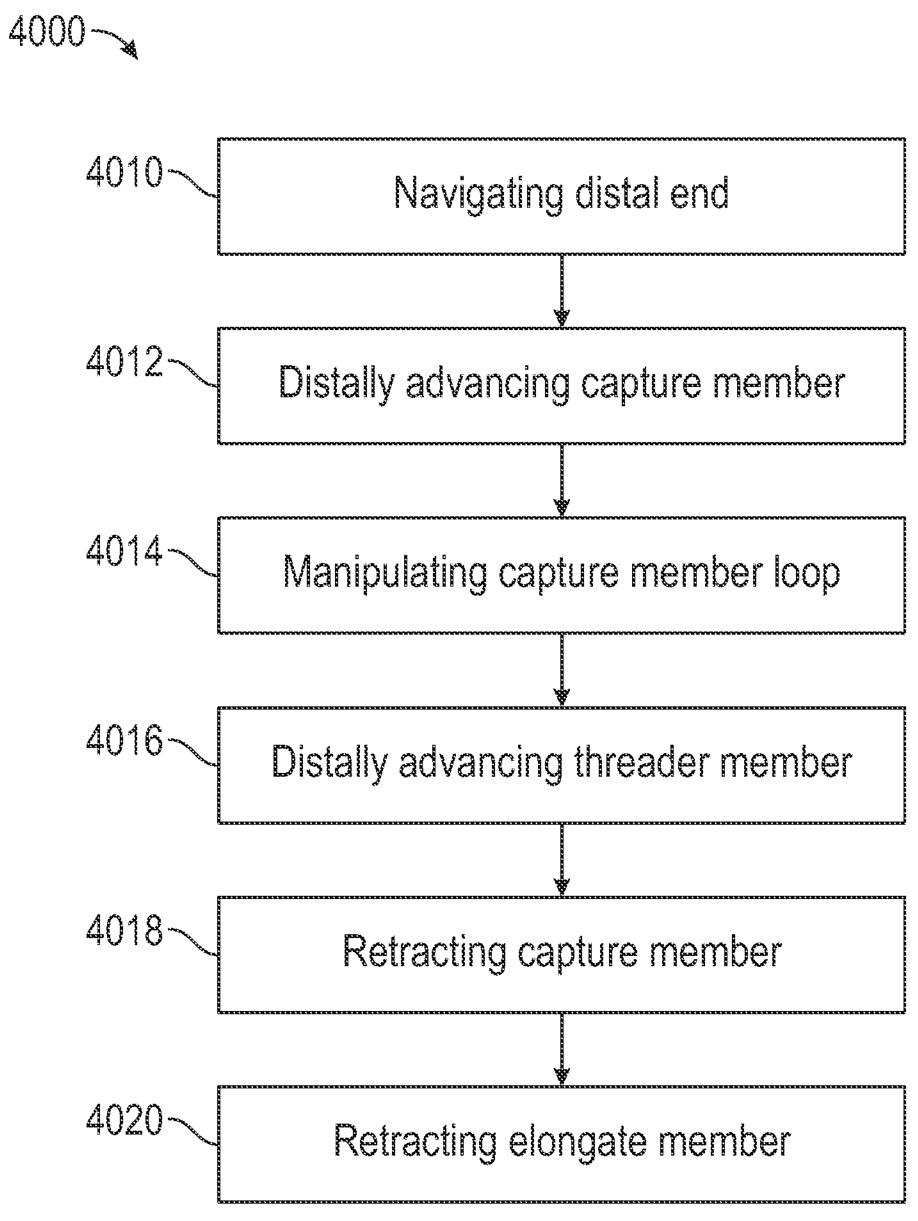
FIG. 11 is a flowchart representation of an example method of retrieving a medical device from the body of an animal.

FIG. 11 illustrates an example method 4000 of retrieving a medical device from the body of an animal. Completion of the method results in removal of the retrieved medical device from the body of the animal.

An initial step 4010 comprises navigating a distal end of a snare according to an embodiment to a location within a vessel within the body of an animal at which a device to be retrieved is located. Another step 4012 comprises distally advancing a capture member of the snare within the elongate member of the snare such that a loop of the capture member exits the elongate member and a portion of the loop lies on a plane that is perpendicular to, or substantially perpendicular to, a lengthwise axis of the elongate member. Another step 4014 comprises manipulating the capture member loop such that a portion of the device to be retrieved is positioned within a throat region of the capture member loop. Another step comprises distally advancing a threader member 4016 of the snare within the elongate member of the snare such that a loop of the threader member passes through the capture member loop. Another step 4018 comprises retracting the capture member within the elongate member of the snare such that the capture member loop tightens around a portion of the device to be retrieved. Another step 4020 comprises retracting the elongate member such that the capture member, threader member, and the device to be retrieved move through the body vessel and exit the body of the animal.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

We claim:

1. A snare, comprising:

an outer sheath defining an outer sheath lumen;

an elongate member disposed in the outer sheath lumen and having a longitudinal axis and at least one elongate member lumen;

a capture member disposed and axially movable within the at least one elongate member lumen, the capture member defining a capture loop having a throat region and an extended portion along a plane that is perpendicular to the longitudinal axis of the elongate member; and a threader member disposed and axially movable within the at least one elongate member lumen, the threader member defining a threader loop.

2. The snare of claim 1, wherein the capture member and the threader member comprise nitinol.

3. The snare of claim 1, wherein the capture member and the threader member comprise stainless steel.

4. The snare of claim 1, wherein the capture member and the threader member comprise stainless steel coated with polytetrafluoroethylene.

5. The snare of claim 1, wherein the outer sheath is adapted to be temporarily locked to the capture member to prevent relative axial movement between the outer sheath and the capture member.

6. The snare of claim 1, wherein the outer sheath comprises a reinforced sheath.

7. The snare of claim 6, wherein in the outer sheath comprises one of a braid and a coil.

8. The snare of claim 1, wherein the at least one elongate member lumen comprises first, second, third, and fourth elongate member lumens.

9. The snare of claim 8, wherein the capture member is disposed within one of the first, second, third, and fourth elongate member lumens; and wherein the threader member is disposed within another of the first, second, third, and fourth elongate member lumens.

10. The snare of claim 8, wherein the capture member defines first and second capture member legs; and wherein the first capture member leg is disposed in the first elongate member lumen and the second capture member leg is disposed in the second elongate member lumen.

11. The snare of claim 10, wherein the capture loop defines a second portion extending from the extended portion and along a plane disposed at a non-parallel and non-orthogonal angle to the longitudinal axis of the elongate member.

12. The snare of claim 10, wherein the threader member defines first and second threader member legs; and wherein the first threader member leg is disposed in the third elongate member lumen and the second threader member leg is disposed in the fourth elongate member lumen.

13. The snare of claim 12, further comprising a handle attached to the elongate member, the handle including a plunger attached to the first and second threader member legs.

14. The snare of claim 13, further comprising at least one pull wire having a first end attached to a first movable component of the handle and a second end attached to a distal end of the outer sheath;

wherein movement of the movable component of the handle results in deflection of the distal end of the outer sheath.

15. The snare of claim 14, wherein the handle further comprises a second movable component that controls movement of the first movable component.

16. The snare of claim 15, wherein the second movable component comprises a control member rotatable along an axis of the handle.

17. The snare of claim 10, wherein the control member defines a frustoconical portion.

18. A snare, comprising:

an outer sheath defining an outer sheath lumen;

an elongate member disposed in the outer sheath lumen and having a longitudinal axis and at least one elongate member lumen;

a capture member disposed and axially movable within the at least one elongate member lumen, the capture member defining a capture loop having a throat region, a first extended portion along a plane that is perpendicular to the longitudinal axis of the elongate member, and a second portion extending from the first portion and along a plane disposed at a non-parallel and non-orthogonal angle to the longitudinal axis of the elongate member; and a threader member disposed and axially movable within the at least one elongate member lumen, the threader member defining a threader loop.

19. A snare, comprising:

an outer sheath defining an outer sheath lumen;

an elongate member having a longitudinal axis and disposed and axially movable within the outer sheath lumen, the elongate member having an elongate member proximal end, an elongate member distal end, and an elongate member main body extending between the elongate member proximal end and the elongate member distal end and having at least one elongate member lumen extending from the elongate member proximal end to the elongate member distal end;

a capture member disposed and axially movable within the at least one elongate member lumen, the capture member having a capture member proximal end and a capture member distal end, the capture member distal end defining a capture loop having a throat region, a first portion extending along a plane that is perpendicular to the longitudinal axis of the elongate member, and a second portion extending from the first portion, the second portion including the capture member distal end and extending along a plane disposed at a non-parallel and non-orthogonal angle to the longitudinal axis of the elongate member;

a threader member disposed and axially movable within the at least one elongate member lumen, the threader member having a threader member proximal end and a threader member distal end, the threader member distal end defining a threader loop, the threader member extending through the capture loop at the first portion; and a handle attached to the elongate member, the handle including a plunger attached to the threader member.

20. A method of retrieving a medical device from the body of an animal, comprising:

navigating a distal end of the snare according to claim 1 to a location within a vessel within the body of the animal at which the device to be retrieved is located;

distally advancing a capture member within the elongate member such that a capture loop exits the elongate member and a extended portion of the capture loop lies on a plane that is perpendicular to the lengthwise axis of the elongate member;

manipulating the capture loop such that a portion of the device to be retrieved is positioned within the throat region of the capture loop;

distally advancing the threader member within the elongate member such that the threader loop passes through the capture loop;

retracting the capture member within the elongate member such that the capture loop tightens around a portion of the device to be retrieved; retracting the elongate member such that the capture member, threader member, and the device to be retrieved move through the body vessel and exit the body of the animal.

* * * * *